(12) United States Patent
Stevenson et al.

(10) Patent No.: US 10,625,084 B2
(45) Date of Patent: Apr. 21, 2020

(54) AIMD RF SWITCH TO CONNECT AN ICD DEFIBRILLATION ELECTRODE CONDUCTOR EITHER TO A FILTER CAPACITOR OR TO AN RF SOURCE CONFIGURED TO DETECT A DEFECTIVE LEAD CONDUCTOR

(71) Applicant: Greatbatch Ltd., Clarence, NY (US)

(72) Inventors: Robert A. Stevenson, Canyon County, CA (US); Keith W. Seitz, Clarence Center, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 16/414,996

(22) Filed: May 17, 2019

(65) Prior Publication Data
US 2019/0351240 A1    Nov. 21, 2019

Related U.S. Application Data

(60) Provisional application No. 62/673,398, filed on May 18, 2018.

(51) Int. Cl.
| | |
|---|---|
| *A61N 1/375* | (2006.01) |
| *H03H 1/00* | (2006.01) |
| *H01G 4/12* | (2006.01) |
| *H01G 4/228* | (2006.01) |
| *H01G 4/35* | (2006.01) |

(52) U.S. Cl.
CPC .......... *A61N 1/3754* (2013.01); *H01G 4/12* (2013.01); *H01G 4/228* (2013.01); *H01G 4/35* (2013.01); *H03H 1/0007* (2013.01)

(58) Field of Classification Search
CPC ........ A61N 1/3754; H01G 4/12; H01G 4/228; H01G 4/35; H03H 1/0007
See application file for complete search history.

(56) References Cited

U.S. PATENT DOCUMENTS

| | | |
|---|---|---|
| 4,424,551 A | 1/1984 | Stevenson et al. |
| 5,333,095 A | 7/1994 | Stevenson et al. |
| 5,896,267 A | 4/1999 | Hittman et al. |
| 5,905,627 A | 5/1999 | Brendel et al. |

(Continued)

OTHER PUBLICATIONS

Extended European Search Report, Application No. 19154697.7, dated Jun. 4, 2019.

*Primary Examiner* — Mark Bockelman
(74) *Attorney, Agent, or Firm* — Michael F. Scalise

(57) ABSTRACT

An RF switchable filter feedthrough housed inside an AIMD is described. The RF switchable filter feedthrough includes an RF switch having a switching pole that is configured to be controlled by an AIMD control signal to switch between first and second throw position. In the first throw position, a conductive leadwire hermetically sealed to and disposed through an insulator is electrically connected to a two-terminal MLCC chip capacitor which in turn is electrically connected to the ferrule. In the first throw position, EMI energy imparted to a body fluid side implanted lead is diverted to the housing of the AIMD by the chip capacitor. In the second throw position, the conductive leadwire is electrically connected to an RF source disposed inside the AIMD housing. In the second throw position, by measuring a reflective return signal from the RF source it can be determined whether the implanted lead has a defective lead conductor.

28 Claims, 10 Drawing Sheets

(56) References Cited

U.S. PATENT DOCUMENTS

| | | |
|---|---|---|
| 5,959,829 A | 9/1999 | Stevenson et al. |
| 5,973,906 A | 10/1999 | Stevenson et al. |
| 6,275,369 B1 | 8/2001 | Stevenson et al. |
| 6,529,103 B1 | 3/2003 | Brendel et al. |
| 6,765,779 B2 | 7/2004 | Stevenson et al. |
| 6,888,715 B2 | 5/2005 | Stevenson et al. |
| 7,038,900 B2 | 5/2006 | Stevenson et al. |
| 8,352,033 B2 | 1/2013 | Kroll |
| 8,700,156 B2 | 4/2014 | Kroll |
| 8,812,103 B2 | 8/2014 | Kroll et al. |
| 8,825,158 B2 | 9/2014 | Swerdlow |
| 9,272,150 B2 | 3/2016 | Kroll et al. |
| 9,427,577 B2 | 8/2016 | Kroll et al. |
| 9,486,624 B2 | 11/2016 | Swerdlow |
| 9,492,659 B2 | 11/2016 | Brendel et al. |
| 9,636,500 B2 | 5/2017 | Swerdlow et al. |
| 9,675,799 B2 | 6/2017 | Kroll et al. |
| 9,757,558 B2 | 9/2017 | Stevenson et al. |
| 9,814,876 B2 | 11/2017 | Swerdlow |
| 9,821,156 B2 | 11/2017 | Kroll et al. |
| 9,827,416 B2 | 11/2017 | Swerdlow |
| 2004/0235549 A1 | 11/2004 | Struble et al. |
| 2007/0123949 A1 | 5/2007 | Dabney et al. |
| 2009/0163980 A1 | 6/2009 | Stevenson |
| 2009/0322632 A1 | 12/2009 | Milosevic |
| 2010/0191236 A1 | 7/2010 | Johnson et al. |
| 2014/0168917 A1 | 6/2014 | Marzano et al. |
| 2015/0217111 A1 | 8/2015 | Stevenson et al. |
| 2016/0301369 A1 | 10/2016 | Heaney et al. |

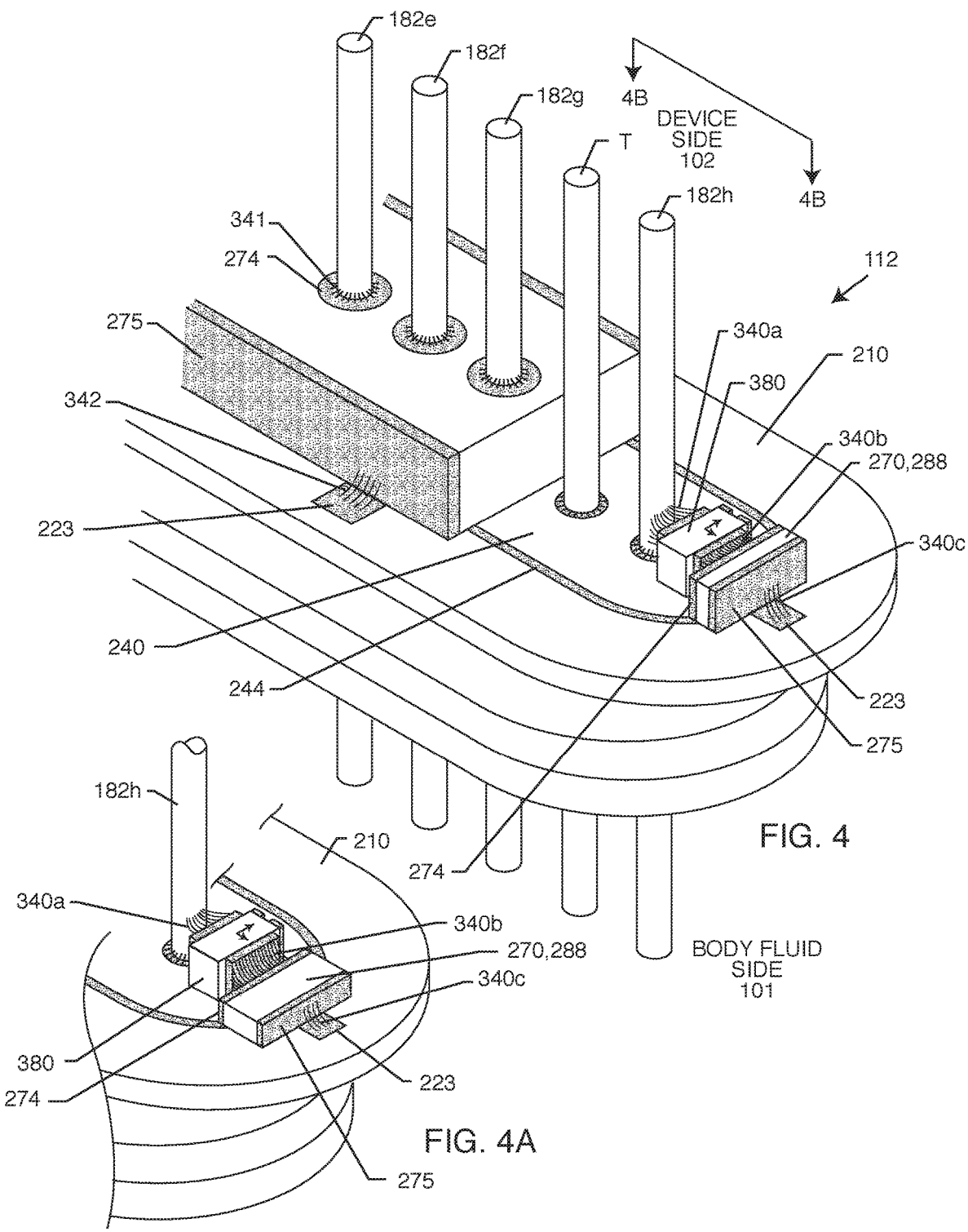

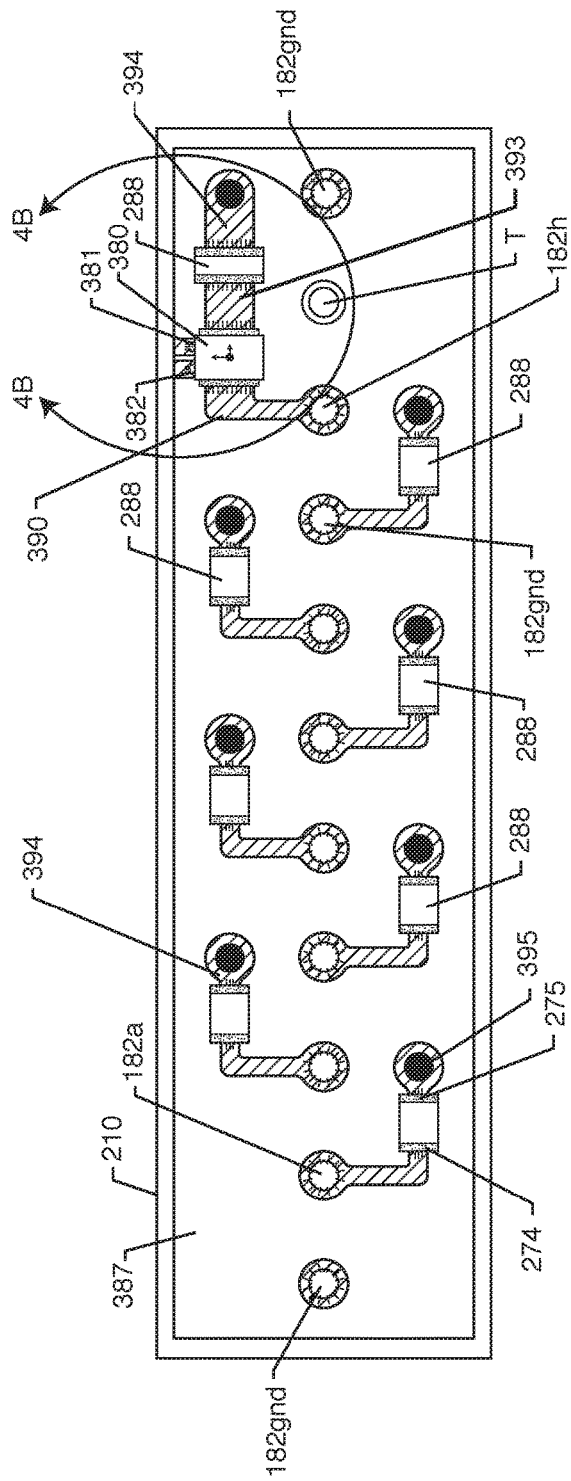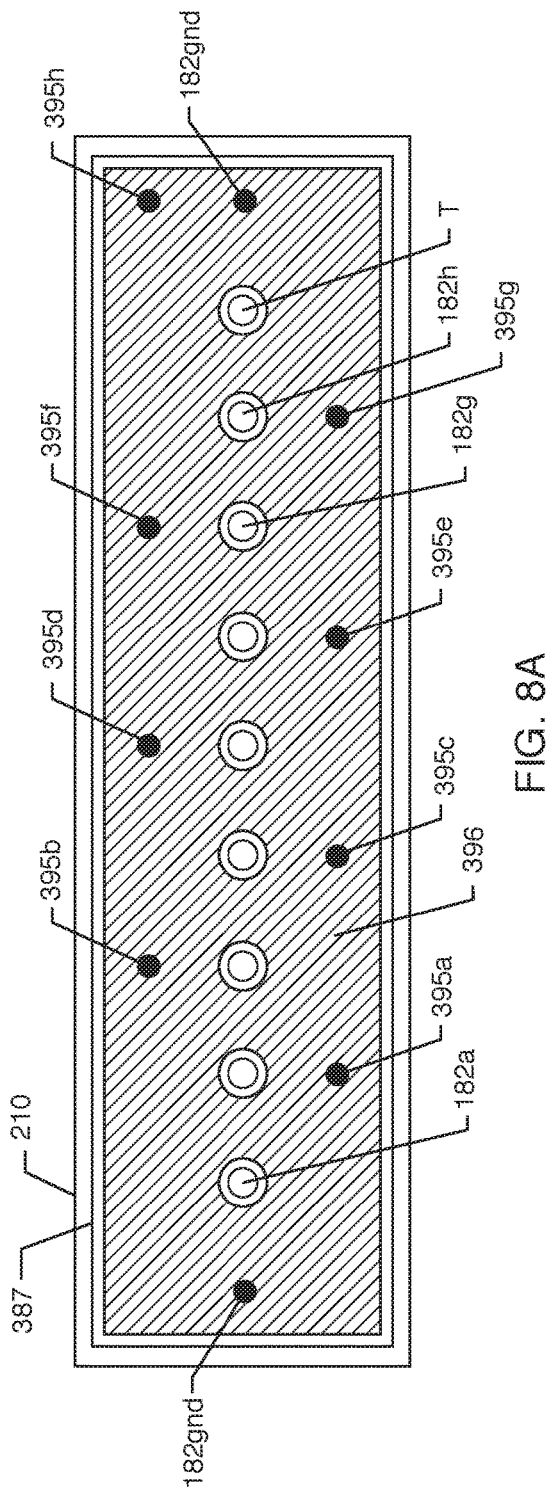

AIMD RF SWITCH TO CONNECT AN ICD DEFIBRILLATION ELECTRODE CONDUCTOR EITHER TO A FILTER CAPACITOR OR TO AN RF SOURCE CONFIGURED TO DETECT A DEFECTIVE LEAD CONDUCTOR

CROSS-REFERENCE TO RELATED APPLICATION

This non-provisional patent application claims priority to provisional application 62/673,398, filed on May 18, 2018, the contents of which are fully incorporated herein with these references.

FIELD OF THE INVENTION

The present invention generally relates to filtered feedthroughs for AIMDs. More particularly, the present invention relates to a novel switch utilizing a two-terminal MLCC chip capacitor such that the switch can be temporarily used for leadwire testing.

BACKGROUND OF THE INVENTION

Patents and patent applications to Charles Swerdlow and/or Mark Kroll, including U.S. Pat. Nos. 9,827,416; 9,821,156; 9,814,876; 9,675,799; 9,636,500; 9,486,624; 9,427,577; 9,272,150; 8,825,158; 8,812,103; 8,700,156 and 8,352,033; U.S. patent application Ser. Nos. 15/810,324; 15/080,343; 15/344,864; 14/224,281 and 14/203,688; PCT Application Nos. PCT/US13/43386; PCT/US13/72957 and PCT/US15/22435; U.S. Provisional Application Ser. Nos. 60/999,041; 61/236,586; 61/689,189; 61/733,713; 61/817,667; 61/834,540; 61/841,107; 62/231,087 and 62/283,104; Foreign Patent Application Ser. Nos. EP2928547A1; EP2859364A1 and EP2854702A1; and their related families are fully incorporated herein by these references. These patents and patent applications are hereinafter referred to as the Swerdlow and Kroll patents.

Additional prior art patents that are also fully incorporated herein by reference include U.S. Pat. Nos. 4,424,551; 5,333,095; 5,896,267; 5,905,627; 5,959,829; 5,973,906; 6,275,369; 6,529,103; 6,765,779; 6,888,715; 7,038,900; 9,492,659 and 9,757,558.

Referring to the '156 and '150 patents, the primary inventive concept was to introduce an RF signal down the lead conductor of the shocking electrode(s) to determine if the electrode has migrated within the patient's body, or if the insulation on the lead conductor has been compromised such as by abrasion, a cut, a break, and the like. The '156 and '150 patents describe that if the shocking electrode migrates too close to the lead conductor or if the insulation on the lead conductor is compromised so that the conductor is exposed to body fluids, during a high voltage shock a large amount of the energy is undesirably dissipated in the wrong area. Consequently, a portion of the high voltage shock is not available to cardiovert the heart, which can lead to death due to ventricular fibrillation.

Inventors Swerdlow and Kroll had conceived of using an RF source and reflective return signal known as the $S_{1,1}$. In network analysis and in using network analyzers, the $S_{1,1}$ signal is known as the reflection signal. By analyzing the reflection signal, one can determine whether the high voltage shocking conductor(s) in the lead body indicates compromised performance. Such compromised performance can be from one or more of the following: undesirable electrode migration toward the edge of the lead body, lead abrasion, or a break in lead insulation. Any one of these undesirable events, whether alone or in combination with each other, can reduce the insulation resistance such that shocking energy is lost. Swerdlow and Kroll spent a great deal of time discussing and trying to figure out how to build an EMI filter that would filter out undesirable EMI signals from the shocking lead, for example, the SVC lead pin #10, while at the same time, allowing the interrogation RF source to pass through. Typically, the RF source that does the $S_{1,1}$ interrogation would be on the order of 125 MHz. The inventors of the present invention pointed out that it would not be possible to design a passive RF filter, such as a feedthrough filter capacitor or a two-terminal MLCC chip capacitor because there are EMI signals involved that are too close in frequency to the $S_{1,1}$ signal. For example, Tetra radios are being introduced into the marketplace that operate at approximately 150 MHz (to as high as 435 MHz).

Worse yet, MRI compatible active implantable medical devices have become very important. They are called MRI conditionally approved devices. Therefore, an ICD or pacemaker in today's marketplace needs to be MRI conditionally approved for both 1.5 Tesla and 3 Tesla MRI scanners. The RF frequency of 1.5 Tesla scanners is 64 MHz and for 3 Tesla scanners is 128 MHz. Since these RF frequencies are relatively close to the RF interrogation $S_{1,1}$ signal, it is difficult to build a filter with a notch ranging from 150 MHz to 435 MHz that is not mistaken for a Tesla scanner frequency.

The inventors of the present invention discussed with Swerdlow and Kroll the possibility of using multi-element low pass filters to create a very sharp cutoff frequency. The inventors analyzed a 7-pole Butterworth filter. The inventors also discussed 5 to 8-pole Tchebycheff filters. These types of filters are capable of providing a relatively sharp cutoff frequency, but one that is not sharp enough to attenuate a 128 MHz MRI signal while passing a 125 MHz $S_{1,1}$ interrogation signal. Furthermore, the high number of elements required for these sharp cutoffs becomes too complicated and too large to fit inside of a modernized ICD. It is difficult enough to fit a single element filter inside an AIMD housing, much less one with 5 to 7 inductor and capacitor elements.

Another problem is that the capacitive elements of the Butterworth and Tchebycheff filter ceramic capacitor-type designs have an aging rate. Even if it were possible to have a sharp enough cutoff to separate a 128 MHz MRI signal from a 125 MHz signals, over time, due to capacitor aging, the Butterworth or Tchebycheff filter characteristic curves would change and their drift might lead then to overlap with the frequency that is intended to be cutoff. In other words, the use of sharp cutoff or notch filters is simply not practical.

Accordingly, the inventors of the present invention have conceived of a novel RF switch that in the normal operating mode is configured to switch the desired conductor pin directly to a filter capacitor, for example a two-terminal MLCC chip capacitor, which is in turn connected to a ferrule ground. In this way, a high degree of EMI filtering is provided to a shocking electrode conductor through the RF switch to the passive EMI filter.

SUMMARY OF THE INVENTION

An exemplary embodiment of the present invention is an RF switchable filter feedthrough 112 for an active implantable medical device (AIMD) 100, the filter feedthrough comprising: a) an electrically conductive ferrule 210 configured to hermetically seal an opening 104 of a housing 103 of the AIMD, the ferrule configured to separate a body fluid side 101 opposite a device side 102, the ferrule including a ferrule opening 212 extending between and to the body fluid side and the device side, wherein, when the ferrule is attached to the opening of the housing of the AIMD, the body fluid side resides outside the AIMD housing and device side resides inside the AIMD housing; b) an insulator 240 hermetically sealing the ferrule opening, the insulator configured to separate the body fluid side and the device side; c) a first conductive pathway 181, 182 hermetically sealed to and disposed through the insulator between the body fluid side and the device side, the first conductive pathway being in non-electrically conductive relation with the ferrule; d) an RF switch 380 disposed on the device side, the RF switch comprising: i) a first electrical connection 383 electrically connected to the first conductive pathway; ii) a second electrical connection 386 electrically connected to a first filter capacitor 270; iii) a third electrical connection 385 configured to be electrically connected to an RF source 381 disposed on the device side of the housing of the AIMD; iv) a fourth electrical connection 384 configured to be electrically connected to an AIMD control signal 382 disposed on the device side of the housing of the AIMD; and v) a switching pole 399 configured to be controlled by the AIMD control signal to switch between a first throw position and a second throw position, wherein the switching pole in the first throw position electrically connects the first electrical connection to the second electrical connection wherein the third electrical connection is not electrically connected to the first electrical connection, and wherein the switching pole in the second throw position electrically connects the first electrical connection to the third electrical connection wherein the second electrical connection is not electrically connected to the first electrical connection; e) wherein the first filter capacitor is disposed on the device side, the first filter capacitor comprising at least one active electrode plate 272 disposed parallel and spaced from at least one ground electrode plate 273, wherein the at least one active and ground electrode plates are disposed within a capacitor dielectric 271; and f) wherein the at least one ground electrode plate of the first filter capacitor is electrically connected to the ferrule and/or housing of the AIMD.

In other exemplary embodiments, the first conductive pathway may be configured to be connected to a high-voltage shocking lead 150 disposed on the body fluid side. The AIMD may be an active implantable cardioverter defibrillator.

The first filter capacitor may comprise a capacitor active metallization 274 electrically connected to the at least one active electrode plate and in non-electrically conductive relation with the at least one ground electrode plate, and a capacitor ground metallization 275 electrically connected to the at least one ground electrode plate and in non-electrically conductive relation with the at least one active electrode plate. The first filter capacitor may be a two-terminal MLCC filter capacitor 288.

A second conductive pathway 181, 182 may be hermetically sealed to and disposed through the insulator between the body fluid side and the device side, the second conductive pathway being in non-electrically conductive relation with the ferrule. A second filter capacitor 270 may be disposed on the device side, the second filter capacitor comprising at least one active electrode plate 272 disposed parallel to and spaced from at least one ground electrode plate 273, wherein the at least one active and ground electrode plates are disposed within a capacitor dielectric 271. The second conductive pathway may be electrically connected to the at least one active electrode plate of the second filter capacitor, and wherein the at least one ground electrode plate of the second filter capacitor is electrically connected to the ferrule. The second filter capacitor may be a feedthrough capacitor 284. Alternatively, the second filter capacitor may be a two-terminal MLCC chip capacitor 288.

The first filter capacitor and RF switch may be disposed upon a circuit board 387, the circuit board disposed on the device side.

The RF switch may be a single-pole double-throw switch or a double-pole double-throw switch.

As shown in FIG. 3A, the RF switch may comprise a fifth electrical connection 397 electrically connected to at least one of the ferrule and/or the AIMD housing thereby providing a switch ground.

As shown in FIG. 3B, the RF switch may comprise a fifth electrical connection 400 electrically connected to the AIMD control signal thereby providing a second electrical connection to the AIMD control signal.

As shown in FIG. 3C, the RF switch may comprise a fifth electrical connection 400 electrically connected to the AIMD control signal thereby providing a second electrical connection to the AIMD control signal, and a sixth electrical connection 401 electrically connected to the RF source thereby providing a second electrical connection to the RF source, and a seventh electrical connection 397 electrically connected to at least one of the ferrule and/or the AIMD housing thereby providing a switch ground.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 4 is an isometric view of the structure of FIG. 3;

FIG. 4A is a sectional view similar to FIG. 4 now showing the capacitor in a different mounting configuration;

FIG. 8 is a top view similar to FIGS. 3, 4B and 6 but showing another embodiment of a circuit board having respective two-terminal MLCC chip capacitors disposed thereon for the leadwires, including the novel switch of the present invention; and FIG. 8A is a top view through a ground electrode plate that would be disposed within the circuit board from the structure shown in FIG. 8, the ground electrode plate grounding the plurality of two-terminal MLCC chip capacitors to the ferrule.

DETAILED DESCRIPTION OF THE PREFERRED EMBODIMENTS

Figure 1:
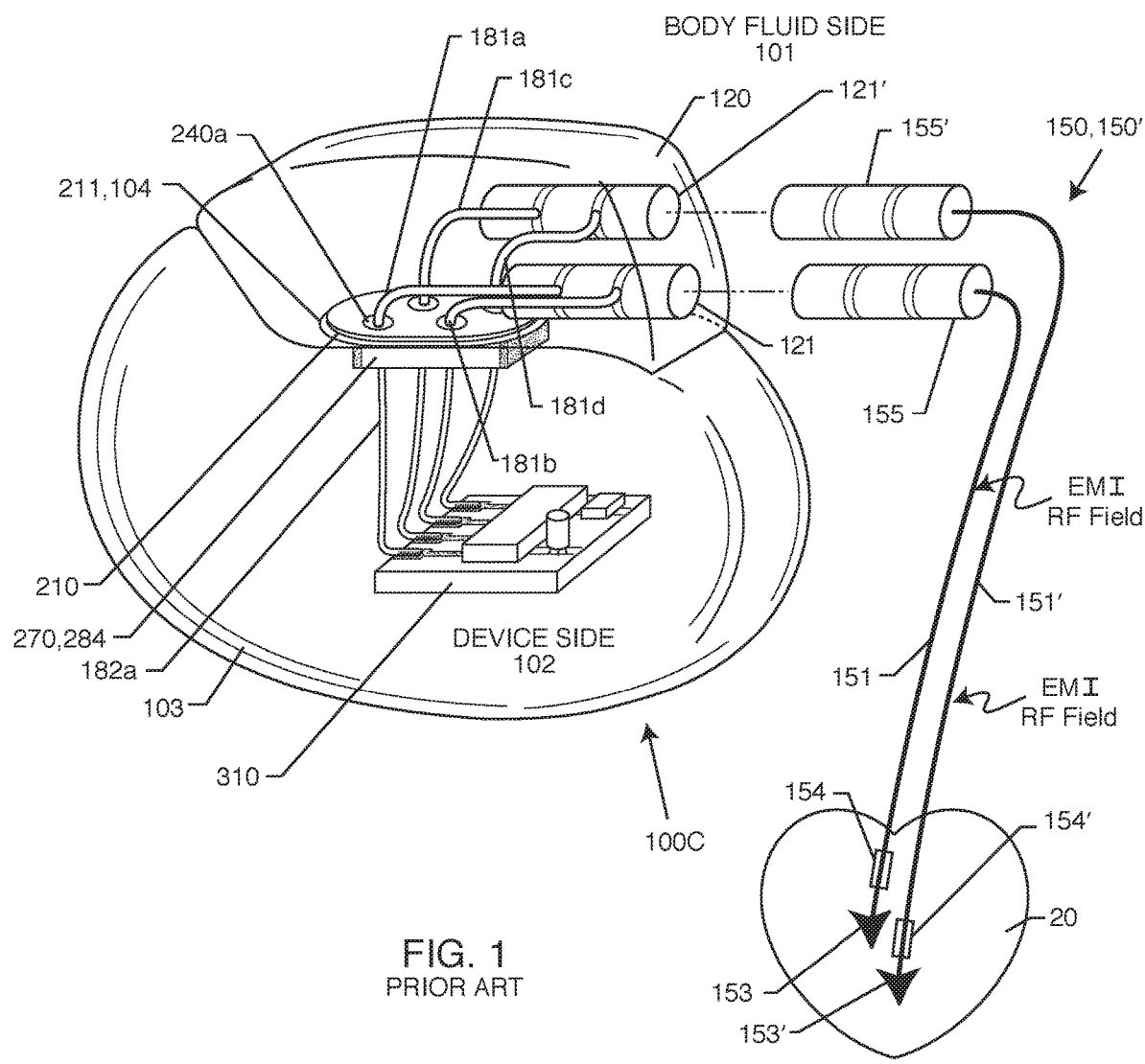
FIG. 1 is a prior art representation of a cardiac pacemaker connected to a heart of a patient.

FIG. 1 is a perspective view of an active implantable medical device (AIMD) known as a cardiac pacemaker 100C. The present invention is directed to implantable cardioverter defibrillators, but FIG. 1 is useful because a cardioverter defibrillator and a cardiac pacemaker have a lot in common. Referring once again to FIG. 1, one can see that the pacemaker 100C has a header block 120, which is typically made of a plastic material such as Tecothane™. The area of the header block is not hermetically sealed. There is a ferrule 210 and, in this case, four insulators 240*a-d*, which are hermetically sealed to the ferrule, and their corresponding leadwires 181*a-d*. Typically, the ferrule is made of titanium and is laser welded 211 into the metallic housing 103 of the AIMD. The metallic housing 103 of a cardiac pacemaker is also typically of titanium. The circuit board 310 is a diagrammatic representation of an AIMD circuit board, which may contain many electronic components, including microprocessors and the like. Leadwires 182*a-d* are generally contiguous with leadwires 181*a-d*. In other words, 181 is the body fluid side portion of the leadwire and 182 is the portion of the leadwire known as the device side (meaning that it is inside the AIMD housing 103). The body fluid side is generally labelled as 101, whereas the device side is generally labelled as 102.

Importantly, the AIMD housing 103 forms an electromagnetic shield thereby protecting sensitive electronic circuits on the circuit board 310 from direct penetration of external electromagnetic fields, also known as electromagnetic interference or EMI. Shown in FIG. 1, electromagnetic interference EMI can couple directly to the implanted leads 150, 150' which for a pacemaker, are generally routed transvenously along conductors 151,151' to distal tip electrodes 153,153' and distal ring electrodes 154,154' that are disposed inside of the human heart 20. Typical cardiac pacemakers have one or more female connector ports 121, 121' formed in the header block into which proximal plugs 155,155' are connected (inserted/plugged) in to. For cardiac pacemaker and ICD applications, having removable plugs is very important as the leadwires 150,150' and their associated electrodes 153,153' and 154,154' are typically implanted for many years (20 years or more). However, the pacemaker 100C has an internal primary battery and depending on whether it's providing constant pacing support or intermittent pacing support, it has a lifetime varying from 4 years to 8-12 years. In other words, AIMDs, also known as devices, go through what's known as device change outs much more frequently than the leads. On the device side shown is a filter 270 that is an externally grounded feedthrough capacitor 284.

Figure 2:
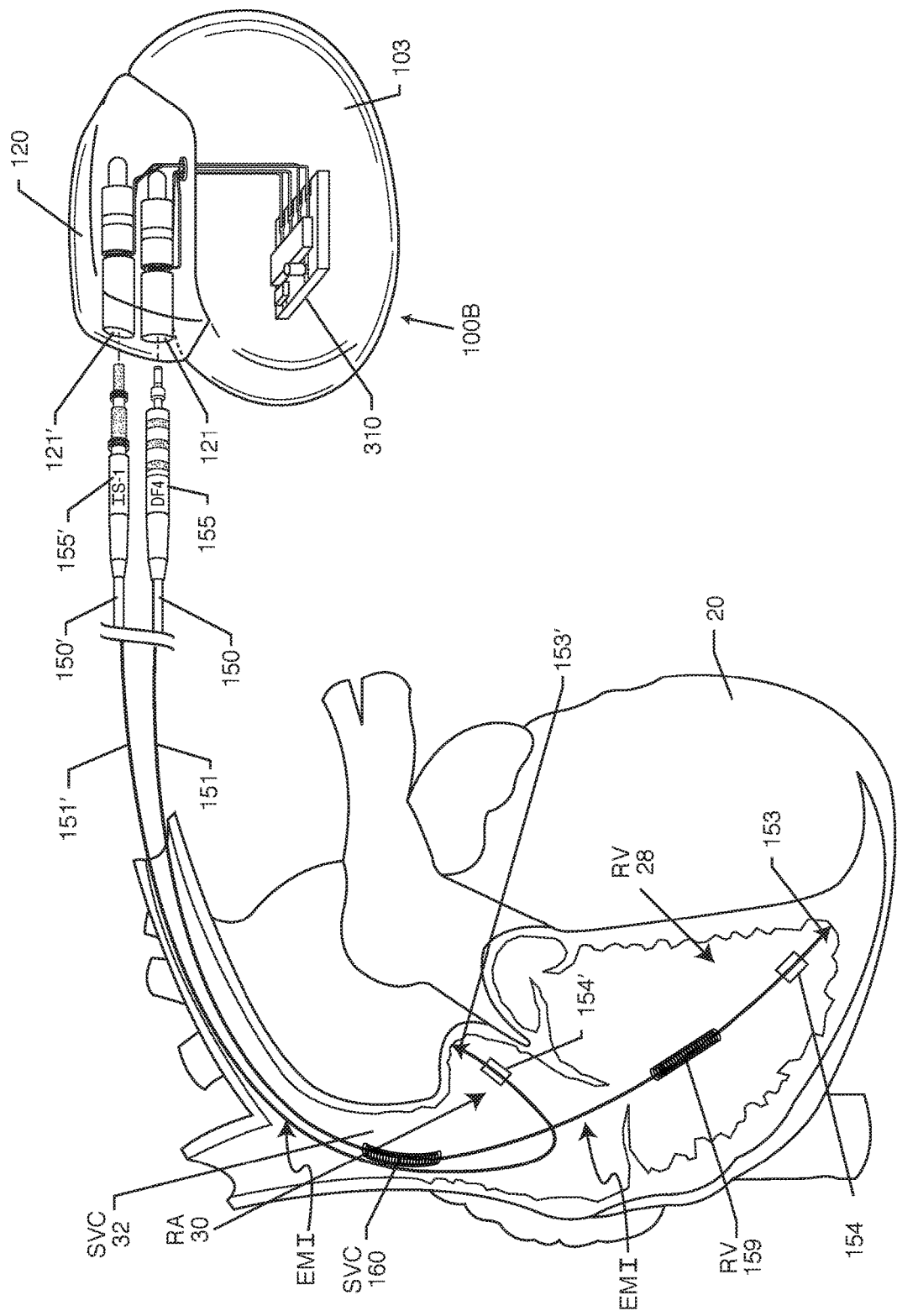
FIG. 2 is another prior art representation of an implantable cardioverter defibrillator connected to the heart of a patient.

FIG. 2 illustrates a sectional-view of a human heart 20 and an AIMD known as an implantable cardioverter defibrillator 100B. In this case, the implantable cardioverter defibrillator or ICD is shown with a DF4 leadwire 150 routed to the right ventricle of the heart and the right atrium. In the industry, this is known as a dual chambered pacemaker and ICD. Referring to the FIG. 2 human heart 20, one can see that there are low voltage electrodes 153 and 154 implanted into the right ventricle. These are known as tip 153 and ring 154 electrodes. There is also an IS-1 leadwire 150', which is a bipolar low voltage lead that is routed into the right atrium 30 thereby, providing pace and sense electrodes in the right atrium 30 with 153' being the tip electrode and 154' being the ring electrode. The DF4 connector provides two high-voltage shocking circuits that run to a high-voltage shock electrode in the Superior Vena Cava (SVC) labeled as element 160. There is a second shocking electrode in the right ventricle (RV) shown as shock electrode 159. It is not always the case that there are two shock electrodes because the ICD housing 103 can also be configured to be a shocking electrode, meaning that shocking vectors may be between the RV and the SVC or between either of the RV and the SVC and the AIMD housing. These are known as shocking vectors and are very important to properly cardiovert the heart in case it's having a dangerous ventricular arrhythmia, otherwise known as ventricular fibrillation. Ventricular fibrillation is immediately life-threatening and, as is commonly known from movies, is corrected when one has seen the external shocking paddles applied to a patient's chest. The ICD of FIG. 2 does the same thing but provides the high-voltage shocks internally to the heart. As illustrated in FIG. 2, EMI can also couple to these implanted leads through antenna action. In this case, the EMI can disrupt the proper operation of the pacemaker, but also could fool the ICD into thinking there was a dangerous ventricular arrhythmia, causing it to deliver what's known in the industry as an inappropriate high-voltage cardioversion shock. High-voltage cardioversion shocks are very painful to the patient and are highly undesirable.

Referring now back to FIG. 1, attention is drawn to the EMI feedthrough filter capacitor 270,284 which is mounted adjacent to the hermetic seal ferrule 210. Feedthrough capacitors are well known in the prior art and are very effective at diverting undesirable EMI at the point of ingress into the AIMD housing 103 to the ferrule and in turn, to the AIMD housing 103. The AIMD housing 103 forms a Faraday shield cage and becomes a system ground. Accordingly, these unwanted EMI signals are diverted to the shield housing 103 such that they cannot interfere with sensitive electronic components on circuit board 310.

Figure 3:
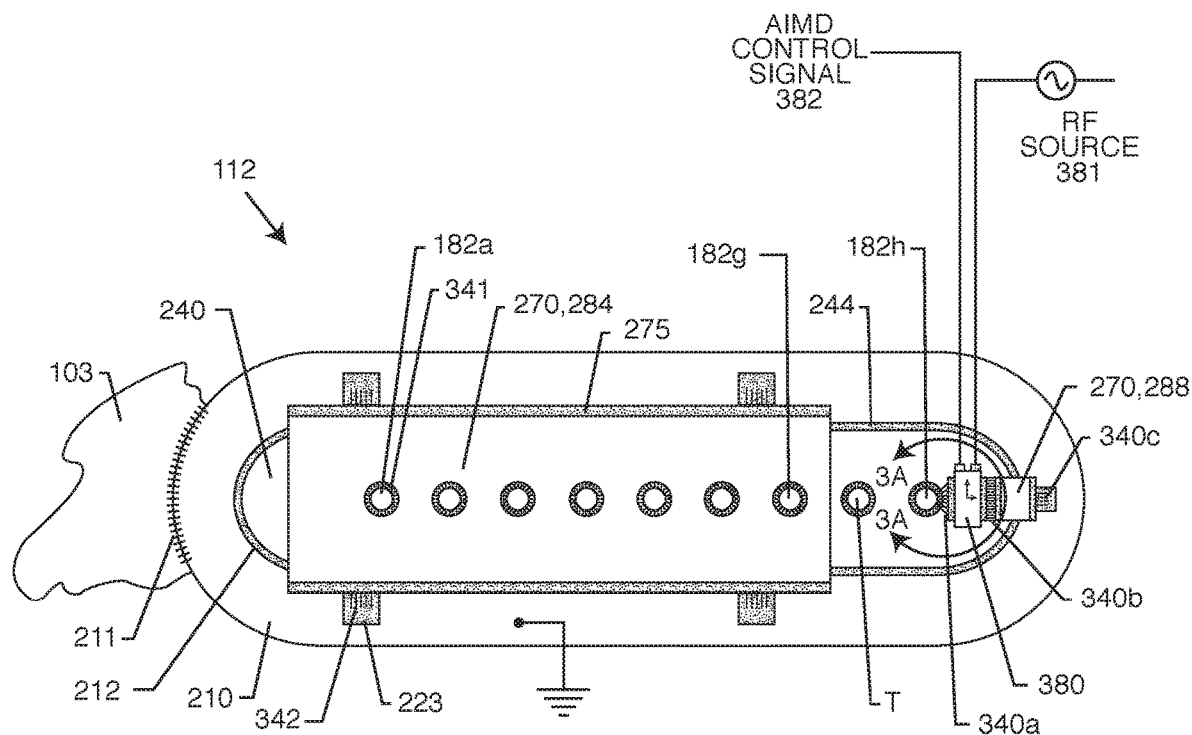
FIG. 3 is a top view of a novel embodiment of the present invention showing a switch disposed on the device side connected to a two-terminal MLCC chip capacitor.

FIG. 3 illustrates a top view from the inside of the AIMD (device side) of a 7-pole feedthrough capacitor 270, 284. The feedthrough capacitor is disposed over and/or adjacent to at least one of the ferrule 210 and the hermetic seal insulator 240. The insulator 240 is generally of either an alumina ceramic or a glass seal, such that it hermetically seals the ferrule and the leadwires. In the prior art, the feedthrough capacitor 270, 284 of FIG. 3 would also encompass a terminal pin 182*h*, which in this case, is a right ventricle high-voltage shocking lead. However, as has been described, it is highly desirable to be able to test the right ventricle high-voltage shocking lead 182*h* and its associated electrodes with an RF source 381. By using an RF source 381 and measuring the reflective return signal known as $S_{1,1}$, inventors Swerdlow and Kroll teach that one can determine whether this critically important implanted lead has a defective or low insulation resistance conductor. It is otherwise very difficult to detect because this particular shocking coil is not always in direct contact with myocardial tissue. For example, the shocking coil 160 is literally floating in the blood pool in the Superior Vena Cava. Sometimes the shocking coil 160 (FIG. 2) is overgrown by what is called tissue encapsulation, but not always. Therefore, it is very hard to know in advance what the state of the shocking coil 160 is until one tries to deliver a high-voltage shock, which means it might fail depending on whether the lead conductor's integrity has been maintained.

FIG. 3 illustrates a very novel way to provide both EMI filtering and to selectively disconnect the EMI filtering and instead connect it to an RF source 381 internal to the AIMD to make routine checks of the SVC high-voltage shocking leadwire conductor integrity. As previously described, Swerdlow and Kroll in their fully incorporated patents teach how to use the RF signal, but they do not provide any description how to also provide EMI protection for this lead. In other words, if EMI protection is not supplied to the RV shocking coils leadwire 182*h*. The leadwire 182*h* can allow EMI to enter into the inside of the AIMD housing 103 where one gets the highly undesirable effect known to EMI engineers as the "genie-in-the-bottle". What "genie-in-the-bottle" means is that once undesirable EMI energy is inside the AIMD housing, it can cross-couple through either antenna action, mutual capacitance or mutual inductance to other circuits, such as sensitive sense circuits, which could disrupt the proper operation of either the pacemaker sensing circuits of the ICD or worst yet, the high-voltage shocking circuits of the ICD.

Referring back now to FIG. 3, one can see that a novel RF switch 380 has been provided. In the normal operating position, the RF switch 380 is connected to a filter capacitor 270, which in this case or in this embodiment, is shown as a two-terminal MLCC chip capacitor 288. Importantly, the two-terminal MLCC chip capacitor 288 is located very close to the RF switch and very close to the right ventricle leadwire 182*h*, such that there is minimal undesirable inductance in the circuit. In other words, this allows the two-terminal MLCC chip capacitor 288 to be a very effective EMI filter. It is understood to those skilled in the art that the chip capacitor 270, 288 illustrated in FIG. 3 could be a two-terminal MLCC chip capacitor (multilayer ceramic capacitor), stacked tantalum or any other two-terminal capacitor technology.

In an embodiment, three-terminal feedthrough capacitors or the two-terminal MLCC chip capacitors of the present invention would be designed for high power MRI applications and have a dielectric constant (k) of either less than 1,000 or less than 200. AIMD primary filter capacitors having a dielectric constant less than 200 are described in U.S. Pat. Nos. 9,764,129 and 9,014,808, the contents of which are fully incorporated herein by reference. AIMD primary filter capacitors having a dielectric constant less than 1,000 are described in U.S. Pat. No. 9,757,558, the contents of which is fully incorporated herein by reference. In another embodiment, the dielectric constant would be 500 plus or minus 50. In yet another embodiment, the dielectric constant is 500, plus or minus 100.

Referring again to FIG. 3, one can see that there is a control signal 382 that comes from an AIMD internal circuit board or circuit such that the AIMD control signal, either at a preset interval or upon command, can disconnect the RF switch from being in electrical contact with the two-terminal MLCC chip capacitor 270, 288 and connect the RF switch to an internal RF source 381. As previously described, that is for the purpose of testing the electrical integrity of an implanted lead. Importantly, testing of the implanted lead by the RF source 381 is generally for a period of a few milliseconds, but less than 1 second. That is so that during testing there is very little chance of an EMI signal disrupting the internal electronic circuitry.

Figure 3A:
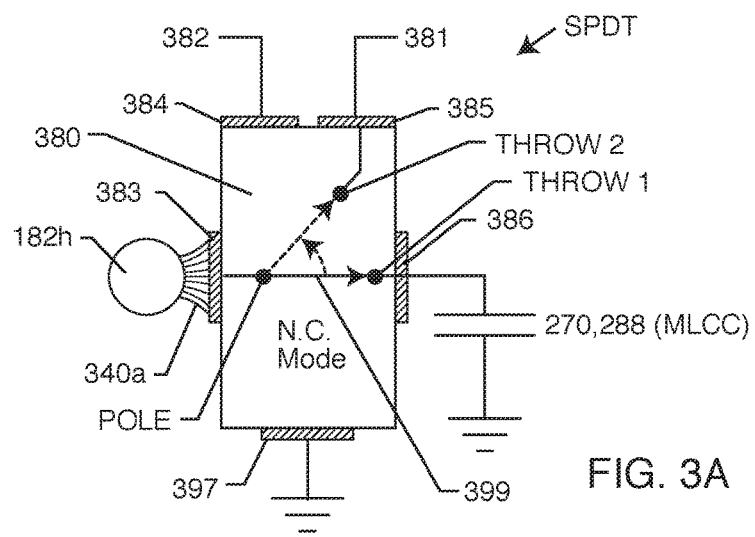
FIG. 3A is an enlarged view of the novel switch of FIG. 3.

FIG. 3A, which is an enlarged view taken from section 3A-3A of FIG. 3, shows the normally closed (N.C.) position of the RF switch 380. In this case, there is a wiper 399 with an arrow head. The POLE of switch 380 is electrically connected to termination pad 383 and through electrical connection material 340*a* to the leadwire 182*h*. In FIG. 3A, one will see that the switch pole 399 is indicated. The normally closed pole 386 is also shown as Throw 1. Once the RF switch 380 receives a control signal 382, internal circuits within the electronic switch (not shown) direct the switch to move from its normally closed (N.C.) position to the dashed-line position indicated as Throw 2. This disconnects the (two-terminal MLCC chip capacitor) filter capacitor 270, 288 and at the same time electrically connects the terminal pin 182*h* to the RF test signal source circuit 381. To those skilled in the art, in the vernacular of electronic switches, the electronic switch 380 of FIG. 3A is known as a single-pole double-throw (SPDT) switch.

Referring once again to FIG. 3A, with the RF switch 380 in the normally closed position, if one attempts to inject an RF source into the system, the RF signal would be diverted (filtered) by the two-terminal MLCC chip capacitor 270, 288 to ground being the ferrule, the AIMD housing and/or an AIMD internal circuit board ground trace. In other words, the RF signal would not be able to reach a distal defective implanted lead conductor, and in particular, there would be no useful return $S_{1,1}$ signal. The present invention solves this problem by disconnecting the filter 270, 288 while the RF test signal 381 is being delivered. At all other times (normally closed), the RF filter 270, 288 is connected through the RF switch 380 to leadwire 182*h* to provide its vital filtering function.

As shown in FIG. 3A it will be appreciated by those skilled in the art that RF switch 380 may include a termination 397 which is attached to ground thereby providing a switch ground, the ground being the ferrule, the AIMD housing and/or an AIMD internal circuit board ground trace.

Figure 3B:
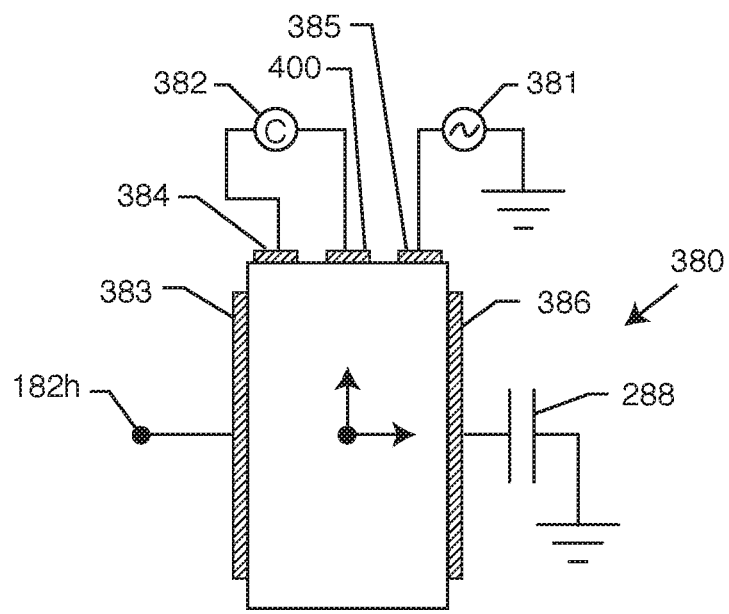
FIG. 3B is a view similar to FIG. 3A showing another embodiment of the novel switch.

Alternatively, as shown in FIG. 3B, the RF switch 380 includes a termination 400 which is electrically connected to the AIMD control signal, thereby providing a second electrical connection to the AIMD control signal 382 that is controlled on the circuit board inside the AIMD housing.

Figure 3C:
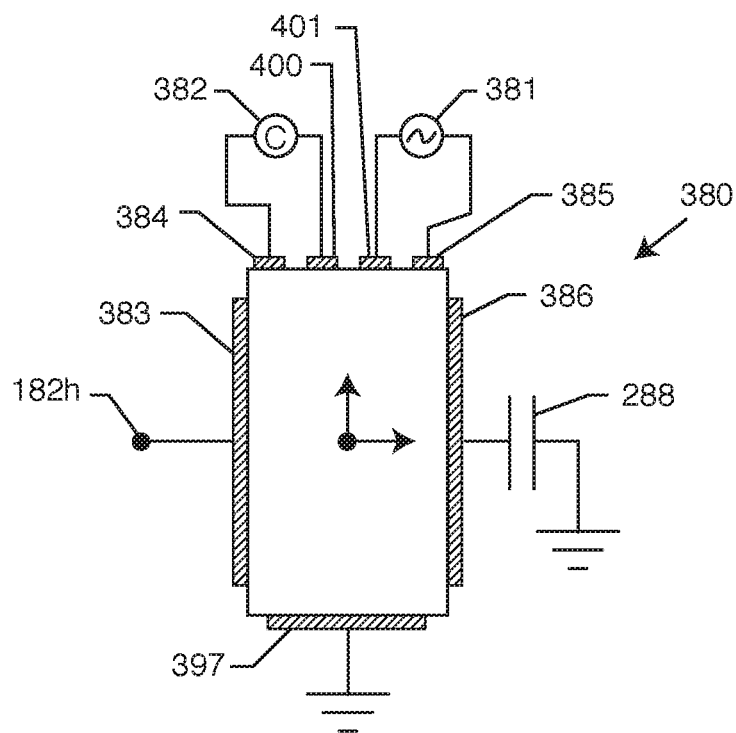
FIG. 3C is a view similar to FIG. 3A showing yet another embodiment of the novel switch.

In another embodiment as illustrated in FIG. 3C, the RF switch 380 includes the termination 400 as in FIG. 3B. However, now the RF switch further includes a termination 401 that is also electrically connected to the RF source 381, thereby providing a second electrical connection to the RF source that is controlled on the circuit board inside the AIMD housing. Also, another electrical termination 397 is attached to ground thereby providing a switch ground, the ground being the ferrule, the AIMD housing and/or an AIMD internal circuit board ground trace.

All modern ICDs have at least one internal circuit board and at least one microprocessor. In general, these microprocessors have programs and are also reprogrammable from what is known in the industry as an external programmer. The purpose of the RF telemetry pin T is to connect to an antenna in the header block 120 (not shown) so that the ICD can communicate with the external programmer. In the present invention, the RF switch is switched from its normally closed position connected to the filter capacitor 270, 288 to a position connected to the RF source 381 in response to a control signal received from ICD electronic circuits which can be from an ICD internal circuit board. The control signal could be a DC bias, a digital signal or a low frequency AC signal. The RF switch control circuitry can be programmed or preset such that the control signal is sent at regular intervals (such as once or twice a day to check the integrity of the lead conductor connected to the shocking coils). Alternatively, the RF switch control circuitry could be programmed with the external programmer to perform this test at other intervals (more or less frequently). An additional feature would be that a health care provider using the external programmer could send the control signal on demand (perform a real time test with the patient present).

It will be understood that at the same time that the control signal is sent that the RF test signal as taught by Swerdlow and Kroll would also be activated. It will be appreciated that the present invention is also applicable to the older style close-coupled wanded telemetry devices. That is where a magnetic coil (aka the hockey puck) is placed upon the patient's chest immediately over the ICD header block which also has a magnetic coil within. This older type of wanded telemetry is effective but has a much lower data transfer rate than the newer RF telemetry systems.

FIG. 4 is an isometric view of the structure of FIG. 3. This figure helps to illustrate the electronic switch 380 attached to the two-terminal MLCC chip capacitor 270, 288. This also shows the electrical connection 340c to a gold bond pad 223. The gold bond pad 223 is gold disposed into a ferrule pocket that is separate from the gold braze 244 forming the hermetic seal between the ferrule 210 and the insulator 240. One can also see the electrical connection 340a from the leadwire 182h to the switch 380. Furthermore, there is an electrical connection 340b between the switch 380 and the capacitor metallization 274 of the two-terminal MLCC chip capacitor 270, 288. In FIGS. 4 (and 4A), the control wires that would be connected to the RF source 381 and the control 382 are not shown for simplicity.

FIG. 4A is very similar to the two-terminal MLCC chip capacitor RF switch illustrated in FIG. 4, except in this case, the two-terminal MLCC chip capacitor is flipped and is lying flat-side or flat-face down against the insulator and/or ferrule. In both cases, as illustrated in FIG. 4 and in FIG. 4A, these two-terminal MLCC chip capacitors are metallized and configured such that they have very low resistance. In FIG. 4A, the active metallization 274 is attached directly to the RF switch 380. Its ground metallization 275 is electrically connected 340c to a gold bond pad 223, as shown. Ferrule gold pocket pads and metal additions provide an oxide-resistant ground connection for the filter capacitor 270, 288 and are more fully described in U.S. Patent Pub. No. 2018/0236244, the contents of which are fully incorporated herein by reference.

FIG. 4A is similar to FIG. 4 in that it shows the novel RF switch 380, but in this case the MLCC chip capacitor 270, 288 is laid down flat on its side. In the art, this MLCC chip capacitor is known as a reverse geometry MLCC chip capacitor or a reverse geometry two-terminal chip capacitor because the active metallization 274 and ground metallization 275 are disposed along its long sides. Other prior art MLCC chip capacitors are typically metallized on their short ends, which provides two problems if used as shown herein. The first problem is that providing the metallization on the short ends means that the capacitor has a much higher internal inductance than a reverse geometry capacitor and, therefore, makes a poorer EMI filter at very high frequencies. Also, because of its narrow geometry, a reverse geometry two-terminal MLCC chip capacitor, as illustrated in FIG. 4A, fits into the tight space between pin 182h and the ferrule 210 much better. Referring back to FIG. 4, the two-terminal MLCC capacitors 270, 288 are known as reversed geometry two-terminal MLCC chip capacitors positioned in the tombstone position. The tombstone position means that the electrode plates are disposed perpendicular to the device side surfaces of the insulator and/or ferrule. In this manner, the capacitor resembles the mounting of a tombstone, thus explaining the tombstone naming description.

It will also be appreciated that filter capacitors other than two-terminal MLCC chip capacitors can be used in combination with the RF switch to provide high frequency EMI filtering. Exemplary alternate capacitors include three-terminal feedthrough capacitors and flat-thru capacitors. Flat-thru capacitors are more fully described in U.S. Pat. No. 8,422,195, the contents of which are herein fully incorporated by reference.

Figure 4B:
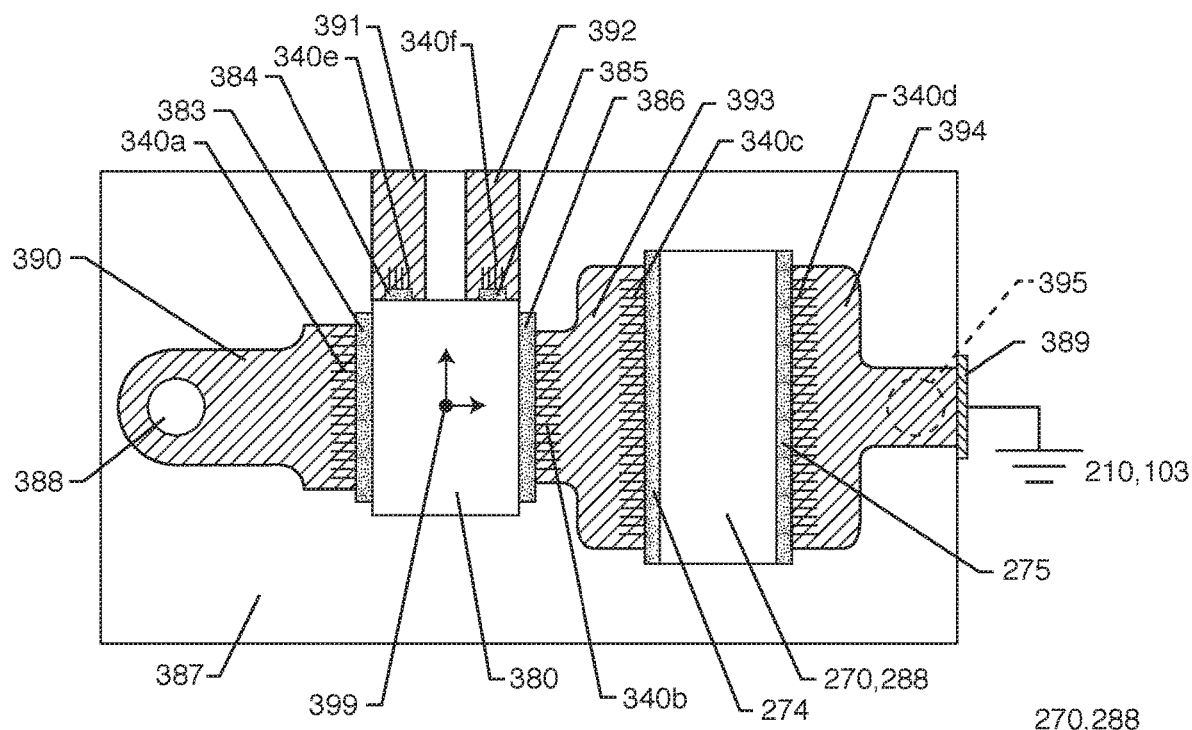
FIG. 4B is a view generally taken from FIG. 4 but now showing a new embodiment where the switch and capacitor are mounted on a circuit board.

FIG. 4B illustrates that the RF switch 380 and two-terminal MLCC chip capacitor 270, 288 of FIGS. 4 and 4A could be first mounted on a circuit board 387. The circuit board 387 has circuit traces and lands disposed on its surface. Alternatively, the circuit traces could be disposed inside of a multilayer board. Via hole 388 is designed to be electrically connected to the terminal pin 182h. The RF switch 380 is shown electrically connected 340a to the circuit trace land 390. The RF switch 380 is also electrically connected to another circuit trace land 393, again, with electrical connection material 340b. Electrical connection material 340c connects land 393 to the active metallization 274 of the two-terminal MLCC chip capacitor 270, 288. There is also another circuit trace 394, which is the ground circuit trace to which the ground termination 275 of the two-terminal MLCC chip capacitor is electrically connected with electrical connection material 340d. The ground circuit trace or land 394 is electrically connected to a circuit board edge metallization 389. This edge metallization would then be connected to either a gold braze 244 or a gold pocket pad 223, as previously illustrated in FIGS. 4 and 4A.

Referring once again to FIG. 4B, an optional ground electrical connection would be a via hole 395. In this case, an edge metallization on the circuit board 389 is not required. Via hole 395 is spatially oriented over either the gold braze 244 that forms the hermetic seal between the insulator 240 and the ferrule 210 or, it is disposed over an oxide-resistant gold bond pad 223. Via hole 395 is filled with an electrical connection material such as a thermal-setting conductive adhesive, a solder, and the like. Those skilled in the art will appreciate that instead of via holes 388 and 395, it is contemplated that solid filled vias in the circuit board could be attached by BGA bumps, anisotropic conductive films, and the like.

Referring back to FIG. 4B, the RF switch 380 has a location for a control wire 384 that is attached through electrical connection material 340e to a circuit board trace or land 391. There is also an electrical connection 340f to circuit trace 392, which would be for the RF test signal. Wires (not shown for simplicity) would connect from these lands 391 and 392 to, for example, an AIMD circuit board, which provides the control signal and the RF test signal. Electrical connection material 340f connects the RF source termination 385 to land 392.

Figure 4C:
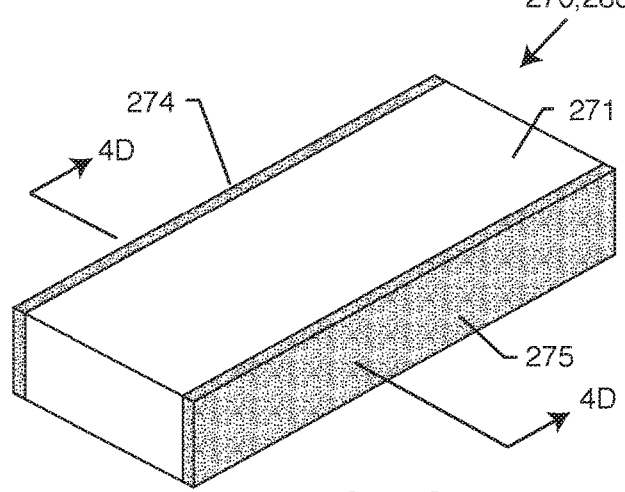
FIG. 4C is an isometric view of a two-terminal MLCC chip capacitor.
Figure 4D:
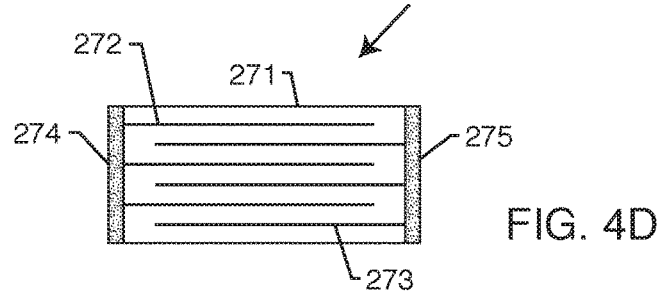
FIG. 4D is a sectional view taken along lines 4D-4D of FIG. 4C.

FIG. 4C is an isometric view of a two-terminal MLCC chip capacitor 288. FIG. 4D is a sectional view taken along lines 4D-4D of FIG. 4C. The capacitor 288 has at least one active electrode plate 272 disposed in a capacitive relationship with at least one ground electrode plate 273. The electrode plates 272 and 273 are disposed within a capacitor dielectric 271. An active metallization 274 disposed on one side of the capacitor is electrically connected to the at least one active electrode plate 272. Similarly, a ground metallization 275 disposed on another side of the capacitor is electrically connected to the at least one ground electrode plate 273. It is understood by those skilled in the art that what is considered the active and ground sides is how the two-terminal MLCC chip capacitor is mounted when in use, as the capacitor can be flipped around and work just the same. The at least one ground electrode plate 273 and the at least one active electrode plate 272 are interleaved (sandwiched) in a capacitive relationship.

Figure 5:
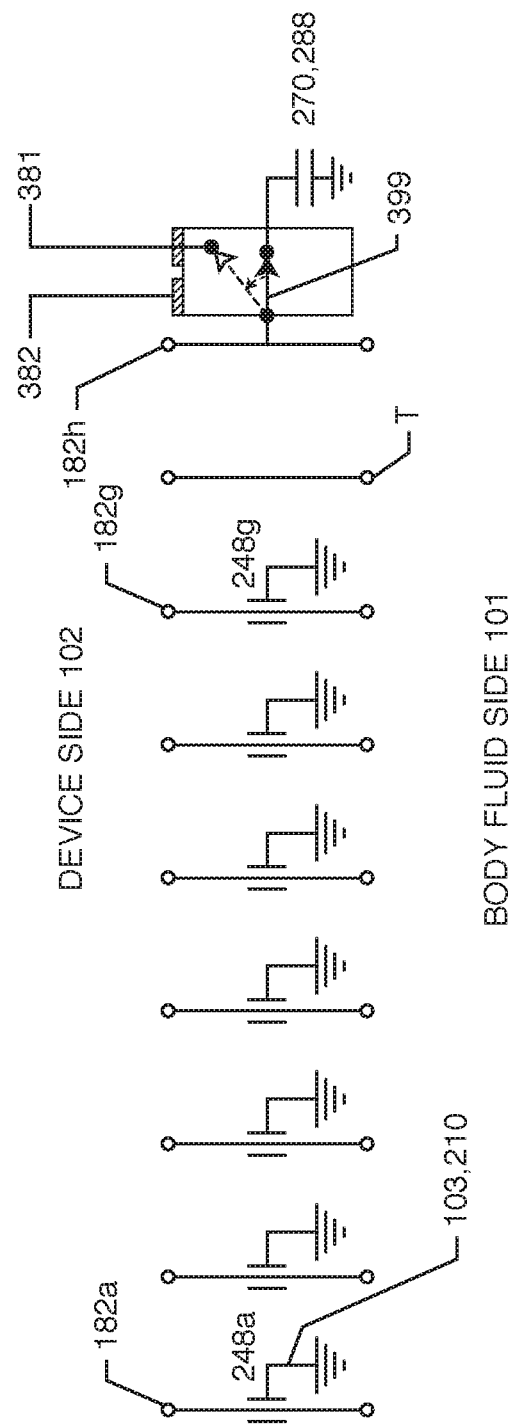
FIG. 5 is the electrical schematic of FIG. 4.

FIG. 5 is an electrical schematic of the filtered hermetic terminals and RF switches previously illustrated in FIGS. 3 and 4. The RF telemetry pin T is not filtered. Terminal pins 182a through 182g are filtered as they pass through the feedthrough capacitor 270, 284. Importantly, FIG. 5 shows the schematic for terminal pin 182h, which is a high-voltage shocking lead that is connected to the RF switch and in turn, to the filtered capacitor 270, 288. Control wire 382 is indicated as well as the RF signal source wire 381.

Figure 6:
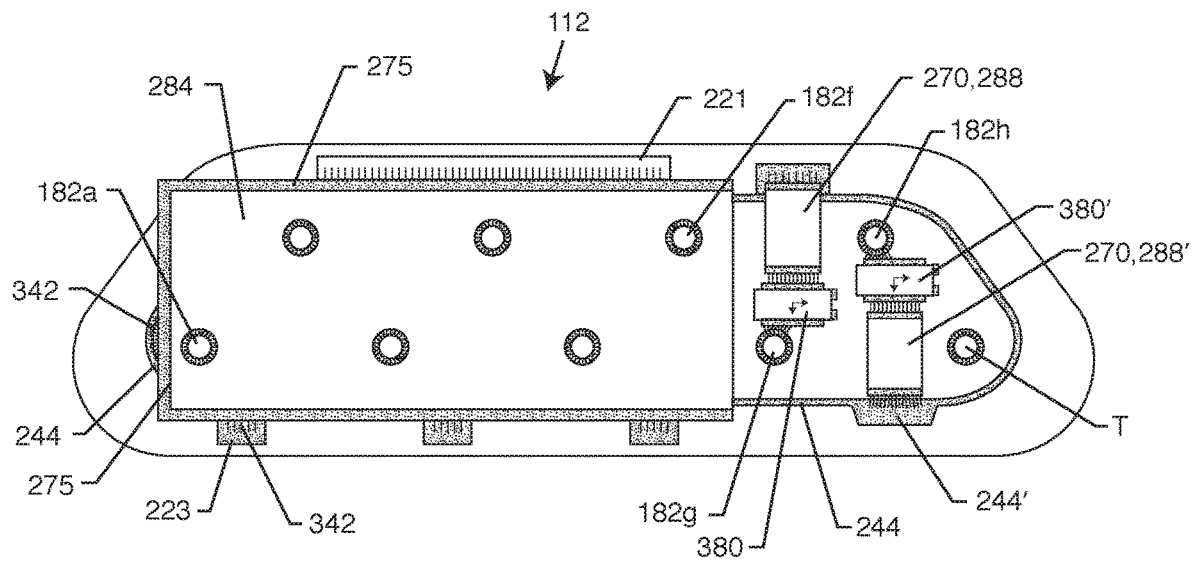
FIG. 6 is another embodiment of the present invention now showing two novel switches and two two-terminal MLCC chip capacitors of the present invention.
Figure 6A:
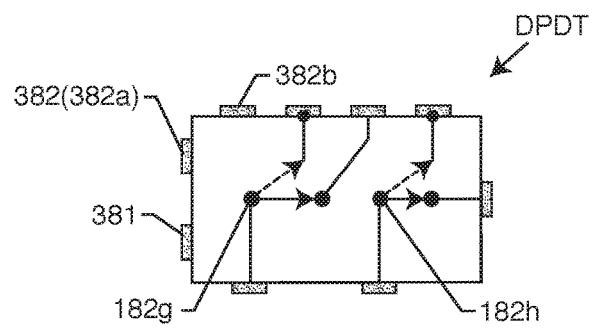
FIG. 6A is an enlarged view of a double-pole double-throw switch that can be used in lieu of the two switches in FIG. 6.

FIG. 6 is very similar to FIGS. 3 and 4, except in this case, there are two RF switches 380 and 380'. There are also two two-terminal MLCC chip capacitors 270, 288 and 270, 288'. In the configuration shown in FIG. 6, this would be in the case where there are shocking electrodes disposed in two locations of the heart, such as the Superior Vena Cava (SCV) 32. So, in this example, leadwire 182g could be connected to the right ventricle 28 shocking coil 159 and leadwire 182h could be electrically connected to the SVC shocking coil 160, which is located above the right atrium 30. It will be appreciated that in FIG. 6, with some minor dimensional adjustments, the RF switch 380 and 380' can be combined into a single RF switch, which is known in the industry as a double-pole double-throw (DPDT) RF switch. A double-pole double-throw RF switch is schematically illustrated in FIG. 6A. The advantage of integrating both switches into a single module is that only one control wire and one other source wire 382 is needed to throw both switches simultaneously. While FIG. 6 shows two shocking coil leads, it is appreciated that the present invention can be used with any number of shocking leads. Referring once again to FIG. 6, it is appreciated that the two two-terminal MLCC chip capacitors 288 and 288' could be integrated into a single monolithic structure.

Referring again to FIG. 6A, it will be appreciated throughout this invention that the RF switch 380 (SPDT and DPDT and other multiple pole switches) have to be either grounded or provided with two control wires 382a and 382b, such that the control signal and RF source are properly biased.

Figure 7:
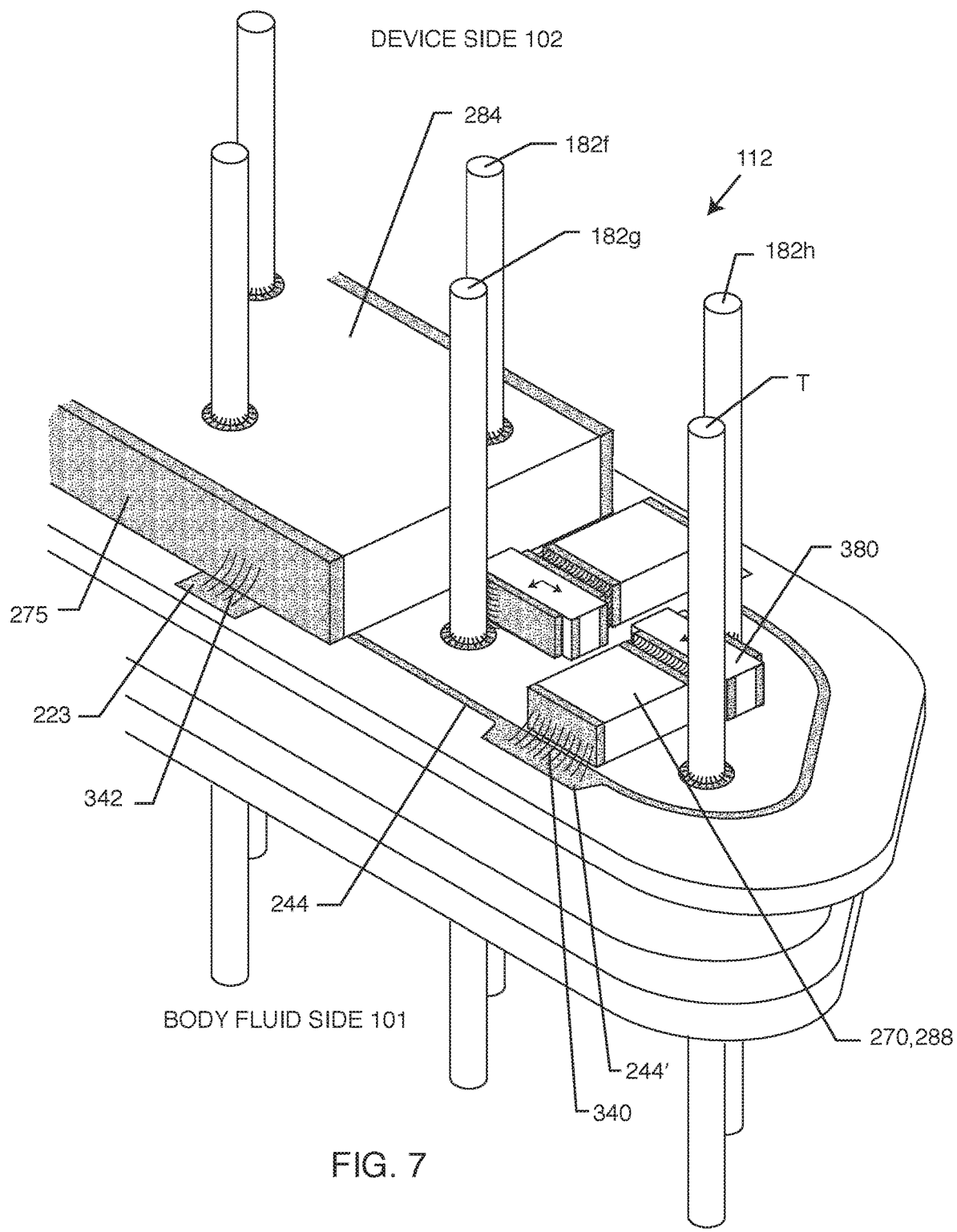
FIG. 7 is an isometric view of the structure of FIG. 6.

FIG. 7 is an isometric view of the structure illustrated in FIG. 6. In this embodiment, rather than using a gold pocket pad, the gold braze hermetic seal 244 has been extended out at location 244'. This area 244' can be a thin layer of gold braze that facilitates the use of an electrically conductive material 340 for attachment.

Referring back to FIG. 6, one can see that a metal addition 221 has been laser welded to the ferrule. The metal addition 221 is of a material that is different in comparison to that of the ferrule and helps provide an oxide-resistant material for electrical attachment. Also shown in FIG. 6 is that the outside ground metallization 275 is disposed on the left-hand side of the capacitor 284. This allows yet another electrical connection to the gold braze hermetic seal 244 to provide a lower inductance connection and improve filter performance. For more information regarding metal additions connected to a ferrule, one is referred to U.S. Pat. No. 9,931,514, the contents of which are fully incorporated herein by this reference.

FIG. 8 illustrates another embodiment of the present invention comprising a circuit board 387 supporting a plurality of filter components. The circuit board may be disposed on at least one of the device side of the insulator or ferrule as shown. Or, the circuit board may be disposed spaced away from the insulator or the ferrule device side. Accordingly, the circuit board may be disposed on, adjacent, near, or even far from the device side of the insulator or ferrule. But, in all cases, the circuit board is disposed inside the AIMD housing. In this case, the feedthrough capacitor 270, 284 had been eliminated. Instead, two-terminal MLCC chip capacitors 288 are disposed adjacent to each of the active leadwires 182a through 182g. The active metallization 274 of each of the two-terminal MLCC chip capacitors 288 is electrically connected through a circuit trace and via hole to the respective leadwires 182a through 182g. It is understood by those skilled in the art that the circuit traces are optional. Instead, the two-terminal MLCC chip capacitors 288 can be rotated such that they make direct contact with their respective leadwire 182a and ground via hole 395. The ground metallization of the two-terminal MLCC chip capacitors is electrically connected to a ground via hole 395, which may be a metallized through-fill or a conductive material filled via hole. These ground via holes 395 are connected to at least one internal circuit board ground plate 396, which is best illustrated in FIG. 8A. The ground plate, in this case, is grounded through two ground pins 182gnd that are either gold brazed, or laser welded to the ferrule 210. It will be appreciated that one, two or even "n" number of ground pins 182gnd can be used such that the ground plate has minimal inductance. As shown, the ground plate 396 has minimal inductance along its length. This is important to ensure that each of the filters 288 has proper high-frequency performance (insertion loss).

For more information regarding circuit board ferrule ground pins, one is referred to (in particular FIG. 83) U.S. Pat. No. 8,195,295, the contents of which are fully incorporated herein by this reference. In accordance with the teachings of U.S. Pat. No. 8,195,295, the circuit board ground plate or ground trace may be: (1) edge grounded to the insulator or ferrule gold braze as shown in FIGS. 54-56; (2) grounded through a via hole to the hermetic seal gold braze as shown in FIGS. 88-93; (3) grounded through a closed via hole to the hermetic seal gold braze as shown in FIG. 94; (4) grounded to a pin laser welded to the ferrule as shown in FIG. 95; (5) grounded to a pin which is gold brazed to the ferrule as shown in FIG. 96; (6) attached to a ferrule projection as shown in FIG. 97; or (7) grounded via a grounding ring as taught in FIGS. 101-102.

Referring once again to FIG. 8, it is noted that the two-terminal MLCC chip capacitors 288 are terminated on their short ends as regular geometry two-terminal MLCC chip capacitors. According to the present invention, however, it is understood that the two-terminal MLCC chip capacitors 288 are preferably reverse geometry capacitors that are terminated on their long ends as taught in FIG. 4A. Referring once again to FIG. 8 the two-terminal MLCC chip capacitor 288 that is associated with the RF switch 380 is shown having a reverse geometry. For more information on reverse geometry capacitors and other two-terminal MLCC chip capacitor mounting techniques, one is referred to FIGS. 22-24 of U.S. Pat. No. 8,195,295 where FIG. 24 shows a reverse geometry two-terminal MLCC chip capacitor with very low inductance $L_3$. The circuit traces of the circuit board of FIG. 8 have been drawn relatively long for simplicity, but it is appreciated that the circuit traces 390, 393, 394 should be as short as possible to minimize undesirable inductance. Undesirable series inductance degrades filter performance at very high frequencies, such as cellular telephone frequencies.

FIG. 8A shows an internal ground plate of the circuit board of FIG. 8. It is understood that the internal ground plate of FIG. 8A could comprise a multiplicity of ground plates or even be an external ground plate or circuit trace. In a preferred embodiment, the internal ground plate is disposed between at least one of the insulator 240 and/or the ferrule 210. The purpose of the ground plate(s) is to shield the RF opening created by insulator 240 thereby preventing direct penetration of radiated electromagnetic interference into the interior of the ICD. These ground plate principles are more clearly taught in U.S. Pat. No. 8,192,295.

Referring now back to FIGS. 8 and 8A, it is apparent that the RF telemetry pin T is not associated with a filter capacitor (RF telemetry pins cannot be filtered or else they would not function properly). Now referring to leadwire 182*h* of FIG. 8, the RF switch 380 of the present invention is shown being electrically connected to the two-terminal MLCC chip capacitor 288, which in turn is connected to the ground plate 396, in this case, through an active circuit trace. This portion of the circuit board 387 has already been described in more detail with reference to FIG. 4B.

Although several embodiments have been described in detail for purposes of illustration, various modifications may be made to each without departing from the scope and spirit of the invention. Accordingly, the invention is not to be limited, except as by the appended claims.

What is claimed is:

1. An RF switchable filter feedthrough for an active implantable medical device (AIMD), the RF switchable filter feedthrough comprising:
   a) an electrically conductive ferrule comprising a ferrule opening extending to a ferrule body fluid side opposite a ferrule device side, wherein, when the ferrule is installed in a housing for an AIMD, the ferrule body fluid and device sides reside outside and inside the housing, respectively;
   b) an insulator hermetically sealing the ferrule opening, the insulator comprising an insulator body fluid side opposite an insulator device side;
   c) a first conductive pathway extending through the insulator to the insulator body fluid and device sides, the first conductive pathway being hermetically sealed to the insulator and in a non-electrically conductive relationship with the ferrule;
   d) a first filter capacitor disposed on, adjacent to or near the ferrule and insulator device sides, the first filter capacitor comprising a capacitor dielectric supporting at least one active electrode plate interleaved in a capacitive relationship with at least one ground electrode plate, wherein the at least one ground electrode plate is electrically connected to the ferrule or is electrically connectable to an AIMD housing; and
   e) an RF switch disposed on the ferrule and insulator device sides, the RF switch comprising:
      i) a first electrical connection electrically connected to the first conductive pathway;
      ii) a second electrical connection electrically connected to the at least one active electrode plate of the first filter capacitor;
      iii) a third electrical connection configured to be electrically connectable to an RF source disposed on the device side of an AIMD housing;
      iv) a fourth electrical connection configured to be electrically connectable to an AIMD control signal disposed on the device side of an AIMD housing; and
      v) a switching pole configured to be controlled by an AIMD control signal to switch between a first throw position and a second throw position, wherein, with the switching pole in the first throw position, the first electrical connection to the first conductive pathway is electrically connected to the second electrical connection to the at least one active electrode plate of the first filter capacitor but not to the third electrical connection to the RF source, and wherein, with the switching pole in the second throw position, the first electrical connection to the first conductive pathway is electrically connected to the third electrical connection connectable to the RF source but not to the second electrical connection to the at least one active electrode plate of the first filter capacitor.

2. The RF switchable filter feedthrough of claim 1, wherein the first conductive pathway is configured to be connected to a high-voltage shocking lead disposed on the ferrule and insulator body fluid sides.

3. The RF switchable filter feedthrough of claim 1, wherein the first filter capacitor comprises a capacitor active metallization electrically connected to the at least one active electrode plate, and a capacitor ground metallization electrically connected to the at least one ground electrode plate.

4. The RF switchable filter feedthrough of claim 3, wherein the at least one ground electrode plate of the first filter capacitor is electrically connected to a gold braze hermetically sealing the insulator to the ferrule.

5. The RF switchable filter feedthrough of claim 1, wherein the first filter capacitor is selected from the group consisting of a two-terminal MLCC chip capacitor, a three-terminal feedthrough capacitor, and a three-terminal flat-thru capacitor.

6. The RF switchable filter feedthrough of claim 1, further comprising:
   a) a second conductive pathway extending through the insulator to the insulator body fluid and device sides, the second conductive pathway being in non-electrically conductive relation with the ferrule; and
   b) a second filter capacitor disposed on the ferrule and insulator device sides, the second filter capacitor comprising a capacitor dielectric supporting at least one active electrode plate interleaved in a capacitive relationship with at least one ground electrode plate,
   c) wherein the second conductive pathway is electrically connected to the at least one active electrode plate of the second filter capacitor, and the at least one ground electrode plate of the second filter capacitor is electrically connected to the ferrule.

7. The RF switchable filter feedthrough of claim 6, wherein the second filter capacitor is selected from the group consisting of a two-terminal MLCC chip capacitor, a three-terminal feedthrough capacitor, and a three-terminal flat-thru capacitor.

8. The RF switchable filter feedthrough of claim 6, wherein the two-terminal MLCC chip capacitor is a reverse geometry two-terminal MLCC chip capacitor.

9. The RF switchable filter feedthrough of claim 1, wherein the first filter capacitor and the RF switch are disposed on a circuit board, and the circuit board is positioned on the device side of the ferrule and the insulator.

10. The RF switchable filter feedthrough of claim 1, wherein the RF switch is a single-pole double-throw switch.

11. The RF switchable filter feedthrough of claim 1, wherein the RF switch is a double-pole double-throw switch.

12. The RF switchable filter feedthrough of claim 1, wherein the RF switch comprises a fifth electrical connection that is electrically connected to the ferrule or is electrically connectable an AIMD housing serving as a switch ground.

13. The RF switchable filter feedthrough of claim 1, wherein the RF switch comprises:
   a) a fifth electrical connection that is electrically connectable to an AIMD control signal thereby providing a second electrical connection to the AIMD control signal;
   b) a sixth electrical connection that is electrically connectable to an RF source thereby providing a second electrical connection to the RF source; and
   c) a seventh electrical connection that is electrically connectable to at least one of the ferrule and an AIMD housing thereby providing a switch ground.

14. The RF switchable filter feedthrough of claim 1, wherein the first filter capacitor has a dielectric constant greater than zero up 1,000.

15. The RF switchable filter feedthrough of claim 1, wherein the at least one ground electrode plate of the first filter capacitor is electrically connected to a gold bond pad disposed into a ferrule pocket.

16. An RF switchable filter feedthrough for an active implantable medical device (AIMD), the RF switchable filter feedthrough comprising:
   a) an electrically conductive ferrule comprising a ferrule opening extending to a ferrule body fluid side opposite a ferrule device side, wherein, when the ferrule is installed in a housing for an AIMD, the ferrule body fluid and device sides reside outside and inside the housing, respectively;
   b) an insulator hermetically sealing the ferrule opening, the insulator comprising an insulator body fluid side opposite an insulator device side;
   c) a first leadwire extending through the insulator to the insulator body fluid and device sides, the first leadwire being in non-electrically conductive relation with the ferrule;
   d) a two-terminal MLCC chip capacitor disposed on the ferrule and insulator device sides, the two-terminal MLCC chip capacitor comprising a capacitor dielectric supporting at least one active electrode plate interleaved in a capacitive relationship with at least one ground electrode plate, wherein the at least one ground electrode plate is electrically connected to the ferrule; and
   e) an RF switch disposed on the ferrule and insulator device sides, the RF switch comprising:
      i) a first electrical connection electrically connected to the first leadwire;
      ii) a second electrical connection electrically connected to the at least one active electrode plate of the two-terminal MLCC chip capacitor;
      iii) a third electrical connection configured to be electrically connectable to an RF source disposed on the device side of an AIMD housing;
      iv) a fourth electrical connection configured to be electrically connectable to an AIMD control signal disposed on the device side of an AIMD housing; and
      v) a switching pole configured to be controlled by an AIMD control signal to switch between a first throw position and a second throw position, wherein, with the switching pole in the first throw position, the first electrical connection to the first leadwire is electrically connected to the second electrical connection to the at least one active electrode plate of the first two-terminal MLCC chip capacitor but not to the third electrical connection to the RF source, and wherein, with the switching pole in the second throw position, the first electrical connection to the first leadwire is electrically connected to the third electrical connection connectable to the RF source but not to the second electrical connection to the at least one active electrode plate of the first two-terminal MLCC chip capacitor.

17. The RF switchable filter feedthrough of claim 16, further comprising:
   a) a second leadwire extending through the insulator to the insulator body fluid and device sides, the second leadwire being in non-electrically conductive relation with the ferrule; and
   b) a second two-terminal MLCC chip capacitor disposed on the ferrule and insulator device sides, the second two-terminal MLCC chip capacitor comprising a capacitor dielectric supporting at least one active electrode plate interleaved in a capacitive relationship with at least one ground electrode plate,
   c) wherein the second leadwire is electrically connected to the at least one active electrode plate of the second two-terminal MLCC chip capacitor, and the at least one ground electrode plate of the second two-terminal MLCC chip capacitor is electrically connected to the ferrule.

18. The RE switchable filter feedthrough of claim 16, wherein the first two-terminal MLCC chip capacitor and the RF switch are disposed on a circuit board, and the circuit board is disposed on, adjacent to, or near the ferrule and insulator device sides.

19. The RF switchable filter feedthrough of claim 16, wherein the RE switch is either a single-pole double-throw switch or a double-pole double-throw switch.

20. The RF switchable filter feedthrough of claim 16, wherein the first two-terminal MLCC chip capacitor has a dielectric constant greater than zero up 1,000.

21. The RF switchable filter feedthrough of claim 16, wherein the at least one ground electrode plate of the first two-terminal MLCC chip capacitor is electrically connected to either a gold bond pad disposed into a ferrule pocket or a gold braze hermetically sealing the insulator to the ferrule.

22. An active implantable medical device (AIMD), comprising:
   a) a housing containing control circuits for the AIMD; and
   b) an RF switchable filter feedthrough disposed inside the AIMD housing, the RF switchable filter feedthrough comprising:
      i) an electrically conductive ferrule comprising a ferrule opening extending to a ferrule body fluid side opposite a ferrule device side, wherein, when the ferrule is installed in a housing for an AIMD, the ferrule body fluid and device sides reside outside and inside the housing, respectively;

ii) an insulator hermetically sealing the ferrule opening, the insulator comprising an insulator body fluid side opposite an insulator device side;
iii) a first lead wire extending through the insulator to the insulator body fluid and device sides, the first leadwire being in non-electrically conductive relation with the ferrule;
iv) a first two-terminal MLCC chip capacitor disposed on the ferrule and insulator device sides, the first two-terminal MLCC chip capacitor comprising a capacitor dielectric supporting at least one active electrode plate interleaved in a capacitive relationship with at least one ground electrode plate, wherein the at least one ground electrode plate is directly electrically connected to the ferrule or is directly electrically connectable to the AIMD housing; and
v) an RF switch disposed on the ferrule and insulator device sides, the RF switch comprising:
A) a first electrical connection electrically connected to the first leadwire;
B) a second electrical connection electrically connected to the at least one active electrode plate of the first two-terminal MLCC chip capacitor;
C) a third electrical connection electrically connected to an RF source disposed on the device side of the AIMD housing;
D) a fourth electrical connection electrically connected to an AIMD control signal disposed on the device side of the AIMD housing; and
E) a switching pole configured to be controlled by the AIMD control signal to switch between a first throw position and a second throw position, wherein, with the switching pole in the first throw position, the first electrical connection to the first leadwire is electrically connected to the second electrical connection to the at least one active electrode plate of the first two-terminal MLCC chip capacitor but not to the third electrical connection to the RF source, and wherein, with the switching pole in the second throw position, the first electrical connection to the first leadwire is electrically connected to the third electrical connection to the RF source but not to the second electrical connection to the at least one active electrode plate of the first two-terminal MLCC chip capacitor.

23. The active implantable medical device of claim 22, wherein the AIMD is an active implantable cardioverter defibrillator.

24. The active implantable medical device of claim 22, wherein the RF switchable filter feedthrough further comprises:
a) a second leadwire extending through the insulator to the insulator body fluid and device sides, the second leadwire being in non-electrically conductive relation with the ferrule; and
b) a second two-terminal MLCC chip capacitor disposed on the ferrule and insulator device sides, the second two-terminal MLCC chip capacitor comprising a capacitor dielectric supporting at least one active electrode plate interleaved in a capacitive relationship with at least one ground electrode plate,
c) wherein the second leadwire is electrically connected to the at least one active electrode plate of the second two-terminal MLCC chip capacitor, and the at least one ground electrode plate of the second two-terminal MLCC chip capacitor is directly electrically connected to the ferrule or is directly electrically connected to the AIMD housing.

25. The active implantable medical device of claim 22, wherein the first two-terminal MLCC chip capacitor and the RF switch of the RF switchable filter feedthrough are disposed on a circuit board, and the circuit board is inside the AIMD housing.

26. The active implantable medical device of claim 22, wherein the RF switch of the RF switchable filter feedthrough is either a single-pole double-throw switch or a double-pole double-throw switch.

27. The active implantable medical device of claim 22, wherein the first two-terminal MLCC chip capacitor of the RF switchable filter feedthrough has a dielectric constant greater than zero up 1,000.

28. The active implantable medical device of claim 22, wherein the at least one ground electrode plate of the first two-terminal MLCC chip capacitor of the RF switchable filter feedthrough is electrically connected to either a gold bond pad disposed into a ferrule pocket or a gold braze hermetically sealing the insulator to the ferrule.

* * * * *